United States Patent [19]

Hutto et al.

[11] 4,160,000

[45] Jul. 3, 1979

[54] EXTRACTION OF HYDROPEROXIDES

[75] Inventors: John F. Hutto; Alfred A. Hoffman, Jr., both of Bartlesville, Okla.

[73] Assignee: Phillips Petroleum Company, Bartlesville, Okla.

[21] Appl. No.: 886,029

[22] Filed: Mar. 13, 1978

[51] Int. Cl.$^2$ .......................................... C07C 179/02
[52] U.S. Cl. .................................................. 568/576
[58] Field of Search ........................ 260/610 A, 610 B

[56] References Cited

U.S. PATENT DOCUMENTS

| 2,430,864 | 11/1947 | Farkas et al. | 260/610 B |
| 2,915,558 | 12/1959 | Alder et al. | 260/610 |

FOREIGN PATENT DOCUMENTS 1151287  5/1969  United Kingdom ................. 260/610 B

*Primary Examiner*—Werren B. Lone

[57] ABSTRACT

A hydroperoxide containing reaction mixture also containing a corresponding unreacted hydrocarbon is treated with an aqueous alcoholic solvent, e.g., aqueous methanolic solvent, to provide in a first step an extract containing a high percentage of hydroperoxide and an appreciable amount of original or unreacted hydrocarbon whereupon the extract is treated with water under recited conditions to obtain two desired phases, one of which is primarily hydrocarbon rejected from the extract by the addition of water and the other an aqueous methanolic solution of the desired hydroperoxide suitable for use in the acid-catalyzed decomposition for the production of carbonyl compounds and hydroxy compounds.

9 Claims, No Drawings

EXTRACTION OF HYDROPEROXIDES

This invention relates to the extraction of hydroperoxides from mixtures containing them. More specifically, it relates to the recovery of hydroperoxides from a reaction mixture in which the hydroperoxide is present together with a corresponding hydrocarbon.

According to a concept of the invention, there is provided a process wherein in a first step aqueous alcoholic solvent, e.g., an aqueous methanolic solvent, is employed to produce two phases; an aqueous phase or extract phase which contains the hydroperoxide which it is desired to recover and an appreciable amount of the original unreacted hydrocarbon and solvent and a second step wherein a limited amount of water is added to said extract to displace therefrom an oily layer which contains only a minor proportion of peroxide and a major proportion of hydrocarbon. A more specific concept of the invention provides a process in which the said limited amount of water added to the extract is an amount broadly between 2 and 50 wt. %, preferably from 5 to 30 wt. % based on the weight of the extract.

Thus, we have discovered that by limiting, as herein described, the amount of water added to the extract we can obtain contrary to the teachings of the art, an oily layer containing only a minor proportion of peroxide while containing a major proportion of hydrocarbon which, of course, means that there will remain in the extract, desirably so, more peroxide to be recovered therefrom after separation of the oily layer.

In U.S. Pat. No. 2,430,864, issued Nov. 18, 1947 to Adalbert Farkas and Arthur F. Stribley, Jr., there is a disclosure which teaches that after separating the aqueous alcohol phase from the hydrocarbon phase in separating a peroxide concentrate, the alcohol phase is subsequently diluted with water to reject an oily layer comprising a major proportion of peroxide and minor proportion of other partial oxidation products and hydrocarbon. The disclosure of the patent is incorporated herein by reference.

An object of this invention is to provide a process for the recovery of hydroperoxides from reaction mixtures containing the same. Another object of the invention is to provide a process for the improved recovery of a hydroperoxide from a reaction mixture in which it has been produced by so operating a two-step extraction process that there will be rejected in a second step an oily layer comprising only a minor proportion of peroxides and a major proportion of hydrocarbon.

Other aspects, concepts, objects and the several advantages of the invention are apparent from a study of this disclosure and the appended claims.

According to the present invention there is provided a process for the recovery of hydroperoxide from a reaction mixture containing the same and unreacted corresponding hydrocarbon from which it has been produced which comprises, in a first step extracting said mixture with an aqueous alcoholic solvent to obtain an extract containing a high percentage of hydroperoxide and, in a second step, adding to said extract an amount of water only sufficient to reject an oily layer containing a minor proportion of hydroperoxide and a major proportion of the hydrocarbon.

In its now preferred form the amount of water added to the extract in the second step, broadly described, will be between from about 2 to about 50 wt. % but preferably will be from about 5 to about 30 wt. % based on the weight of the extract.

The now preferred alcohol is methanol.

The invention will now be further described with reference to the preferred alcohol, namely methanol.

For the first step of the invention we have found that a concentration for the aqueous methanol of about 80–95 wt. % should be employed. Preferably this concentration should be from about 83 to about 92 wt. %. Above the high end of this range the system approaches total miscibility and below the low end of the range the density of the solvent approaches the density of the feed so closely that economical extraction rates cannot be obtained in continuous commercial equipment. The importance of density difference in liquid-liquid extraction is shown by Treybal, "Mass Transfer Operations," McGraw-Hill, pages 375–380. The limiting practical specific gravity difference between the feed and solvent phases is about 0.15–0.20. This density difference is further reduced within the extraction column by partial miscibility of the phases. The specific gravity difference between the feed and 80% methanol is about 0.15 at 20° C.; for 90% methanol the difference is about 0.18.

The invention is concerned with treatment of a hydroperoxide containing reaction mixture in which the principal impurity is the corresponding unreacted hydrocarbon. Such reaction mixtures are conventionally obtained in the preparation of hydroperoxides by the oxidation of hydrocarbons in the presence of an oxygen containing gas with or without added initiators or oxidation catalysts. Such oxidation processes are well known in the art for example, the preparation of cumene hydroperoxide from cumene. From one viewpoint, the process of the invention provides a hydroperoxide containing mixture which is of considerably higher purity on a solvent-free basis than the original crude oxidation reaction mixture. From another viewpoint, the process of the invention provides a hydroperoxide containing mixture suitable for treatment with aqueous mineral acids, e.g., $H_2SO_4$, to provide an acid-catalyzed decomposition of the hydroperoxide to form carbonyl compounds and hydroxy compounds. With regard to the latter viewpoint, the invention provides a significant advantage over the practice of the prior art in that the amount of unreacted hydrocarbon originally present in the crude reaction mixture is greatly reduced in the hydroperoxide mixture taken to the acid catalyzed decomposition reaction zone thereby effecting considerable economy in energy and equipment by said reduced amount of hydrocarbon.

The invention is applicable to the treatment of oxidation reaction mixtures obtained from hydrocarbons, i.e., to organic hydroperoxide containing mixtures in which the hydroperoxide contained therein is represented by the following general formula:

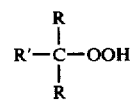

in which R can be hydrogen, or an alkyl radical of 1 to 4 carbon atoms or taken together the R groups can form a cycloalkyl ring of from 4 to 7 carbon atoms, R' can be R or an aryl radical of from 6 to 10 carbon atoms or an alkyl substituted aryl radical of from 7 to about 22 carbon atoms and said hydroperoxides contain from 4 to about 30 carbon atoms per molecule. Preferably the hydroperoxides will have from about 7 to about 24 carbon atoms per molecule.

Examples of specific hydroperoxides which when in admixture with unreacted corresponding hydrocarbon, can be treated according to the process of the instant invention include cyclohexylbenzene hydroperoxide tertiary butyl hydroperoxide, 2-ethyl-2-hexyl hydroperoxide, 2-methyl-2-butyl hydroperoxide, 2,4,4-trimethyl-2-pentyl hydroperoxide, 1-methylcyclohexyl hydroperoxide, cycloheptyl hydroperoxide, α-methyl-benzyl hydroperoxide, α,α-dimethylbenzyl hydroperoxide, 1-phenylcyclohexyl hydroperoxide, benzyl hydroperoxide, 1-phenyl-2-methylcyclopentyl hydroperoxide, and the like.

The crude oxidation reaction mixtures treated according to the instant invention can contain broadly from about 3 to about 80% by weight of the hydroperoxide and preferably from about 10 to about 50 wt. % of the hydroperoxide.

The remainder of the oxidation reaction mixture is essentially the unreacted corresponding hydrocarbon from which the hydroperoxide is derived. Small amounts of other materials or by-products of the oxidation may be present in the crude oxidation mixture.

According to the process to which the invention is applied, the crude hydroperoxide containing mixture described above is treated in a first step with an aqueous methanolic solvent to provide a solvent extract of the hydroperoxide. Said aqueous methanol solvent broadly contains from 80–95 wt. % methanol and preferably from 83–92 wt. % methanol based on the total solvent composition.

The total amount of extraction solvent that is employed to treat the crude hydrocarbon oxidation reaction mixture which contains the hydroperoxide is broadly from 0.5/1 to 20/1 and preferably from 1/1 to 5/1 wherein the above ratios express the weight ratio of extraction solvent to the crude oxidation reaction mixture (feed).

The first step with the solvent with ratios of solvent to feed described above, can be carried out in any manner which is known in the art. The solvent extraction step provides an extract which contains a high percentage of the original hydroperoxide in addition to an appreciable amount of the original unreacted hydrocarbon and the extraction solvent. The material which does not appear in the extract is primarily the unreacted hydrocarbon with small amounts of the hydroperoxide and extraction solvent. It is often convenient to return this material to the oxidation reaction zone.

According to the process of the invention in the second step, the extract of hydroperoxide obtained by using aqueous methanol, as described herein, is further treated with a limited additional amount of water. The total amount of water added to the extract is limited broadly to between 2 and 50 wt. % and preferably is limited to be from about 5 to about 30 wt. % based on the weight of the extract.

The mixing of water with the extract in this step of the instant invention can be conducted in a variety of ways. For example, a single stage contacting zone can be utilized or a plurality of trays in a column can be utilized to obtain the desired mixing of water with the extract.

According to the invention, the addition of water, within the ranges specified above, to the extract will provide two phases, one of which is primarily hydrocarbon which has been rejected from the extract by the addition of water and the other of which is an aqueous methanolic solution of the hydroperoxide suitable for use in the acid-catalyzed decomposition for the production of carbonyl compounds and hydroxy compounds. The latter phase which can be termed a final extract or treated extract contains the hydroproxide in a much higher purity on a solvent free basis than the original extract. Also more of the originally formed hydroperoxide has been recovered. Thus, the process of the instant invention provides for a recovery of 70 to 95% of the original hydroperoxide in the crude hydrocarbon oxidation reaction mixture while at the same time it increases the concentration of the hydroperoxide in the extract up to from 50 to 90%. Compared to the prior teaching of aqueous methanolic extraction of hydroperoxides, the invention provides a further improvement in that the hydrocarbon in the original crude oxidation reaction mixture is separated in a more convenient and economical manner from the hydroperoxide. Specifically, the invention, in the steps provided as described above, avoids the need to distill large amounts of the hydrocarbon from the mixture either before or after the acid-catalyzed decomposition (cleavage) step has been conducted. This feature alone provides a significant economic advantage in the employment of smaller equipment for the cleavage zone and subsequent distillation of the reaction mixture.

EXAMPLE I

Twenty grams of a hydrocarbon (cyclohexylbenzene) oxidation reaction mixture which contained by analysis 16.1 weight percent cyclohexylbenzene hydroperoxide (also named 1-phenylcyclohexyl hydroperoxide) was extracted with 30 grams of an aqueous methanol solvent (10/90 $H_2O/CH_3OH$) at 25° C. from which there was obtained an extract phase weighing 36.95 grams and the residue phase weighing 12.66 grams. Said residue phase contained 0.59 grams of the hydroperoxide by analysis and an estimated 0.38 grams of the solvent which amount was estimated from the phase diagram behavior for this mixture with aqueous methanol of the composition described. This then indicated that 11.69 grams of the residue phase was cyclohexylbenzene and a negligible amount of impurities. The composition of the extract phase was then calculated by difference to indicate 5.09 grams of cyclohexylbenzene and a negligible amount of impurities, 2.63 grams of hydroperoxide and 29.62 grams of the solvent. It can be noted that a loss of 0.39 grams of material occurred during the transfer in the extraction. For purposes of this example, it is assumed that the loss occurred from the extract phase and each component of the extract phase can then be multiplied by the ratio 36.95/37.34 to obtain a normalized composition which is as follows: cyclohexylbenzene 5.04 grams, cyclohexylbenzene hydroperoxide 2.60 grams, and extraction solvent 29.31 grams. It is seen that the purity of the cyclohexylbenzene hydroperoxide extract on a solvent free basis is then 2.60/7.64×100 or 34%.

According to the instant invention, 4.88 grams of water was added to the extract phase and there was obtained a separation into two phases. The lesser phase being essentially the cyclohexylbenzene rejected from the extract phase by the addition of water according to this invention. This phase weighed 4.23 grams and was comprised of 3.74 grams of cyclohexylbenzene, 0.36 grams of cyclohexylbenzene hydroperoxide by analysis, and an estimated 0.13 grams of solvent. The final extract phase or treated extract weighed 37.02 grams and was comprised of 1.30 grams of cyclohexylbenzene, 2.29 grams of cyclohexylbenzene hydroperoxide and 33.43 grams of aqueous methanol. Again, the cyclohexylbenzene hydroperoxide content was determined by analysis. It can be noted that the sum of the hydroproxide contents of the two phases is 2.65 grams which is reasonably close to the original 2.60 grams calculated for the normalized extract. It can be seen that the treated extract or final extract is greatly reduced in cyclohexylbenzene content and the calculated weight percent hydroperoxide on a solvent free basis is 2.29/3.59×100 or 64%. It can also be calculated that 71% of the original cyclohexylbenzene hydroperoxide is now present in the treated extract phase which can be readily utilized in a mineral acid catalyzed decomposition reaction to provide a mixture of cyclohexanone and phenol.

EXAMPLE II

In a manner similar to that carried out in Example I above, 20 grams of crude cyclohexylbenzene oxidation reaction mixture which was the same as that utilized in Example I was treated with 20 grams of a 10/90 water/methanol extraction solvent at 35° C. The initial residue from extraction weighed 14.61 grams and was comprised of 13.21 grams of cyclohexylbenzene, 0.96 grams of cyclohexylbenzene hydroperoxide as determined by analysis, and 0.44 grams of solvent estimated from phase diagram relations. The extract phase was comprised of 3.57 grams of cyclohexylbenzene, 2.26 grams of cyclohexylbenzene hydroperoxide and 19.56 grams of solvent to give a total weight of 25.39 grams. On a solvent free basis, the hydroperoxide content of the extract phase was 2.26/5.83×100 or 39%. Now according to the instant invention, 5 grams of water was added to the extract phase and there was obtained two phases as before in Example I. The rejected phase or residue phase weighed 3.61 grams and was composed of 2.95 grams of cyclohexylbenzene, 0.55 grams of cyclohexylbenze hydroperoxide and an estimated 0.11 grams of extraction solvent. The hydroperoxide content was again determined by analysis. The treated or final extract phase now contained 23.33 grams of extraction solvent (aqueous methanol), 1.75 grams of cyclohexylbenzene hydroperoxide determined by analysis and 0.62 grams of cyclohexylbenzene. However, it can be noted that the sum of weights of the treated extract phase and the rejected phase equals 29.31 grams which differs from the expected weight obtained by adding 5.0 grams to the original extract phase of 25.39 grams or 30.39 grams. This difference of 1.08 grams probably reflects losses in handling and evaporation of solvent. Said hydroperoxide concentration in the treated extract phase is 1.75/2.37×100 or 74% on a solvent free basis. It can be seen then that the hydroperoxide purity (on a solvent free basis) was improved from 39% in the original extract phase to about 74% in the treated extract phase by the addition of water to the original extract phase according to this invention.

Reasonable variation and modification are possible within the scope of the foregoing disclosure and the appended claims to the invention the essence of which is that in a two step process as described for the recovery of hydroperoxide from a reaction mixture containing the same and a hydrocarbon from which the hydroperoxide has been produced there is employed in the second step of the process a limited amount of water as herein described to obtain a oily layer containing only a minor proportion of peroxide and a major proportion of hydrocarbon.

We claim:

1. A process for the recovery of an organic hydroperoxide, said hydroperoxide being represented by the following general formula

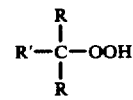

in which R can be hydrogen, an alkyl radical of 1 to 4 carbon atoms, taken together the R groups can form a cycloalkyl ring of from 4 to 7 carbon atoms, R' can be R, an aryl radical of from 6 to 10 carbon atoms, an alkyl substituted aryl radical of from 7 to about 22 carbon atoms and said hydroperoxides contain from 4 to about 30 carbon atoms per molecule from a reaction mixture containing the same and unreacted corresponding hydrocarbon from which it has been produced which comprises, in a first step, extracting said mixture with an aqueous alcoholic solvent having a concentration in the approximate range of 80–95 wt. % alcohol to obtain an extract containing a higher percentage of hydroperoxide and, in a second step, adding to said extract a limited amount of water only sufficient to reject primarily only an oily layer containing a minor proportion of hydroperoxide and a major proportion of the hydrocarbon and an aqueous alcoholic solution phase containing hydroperoxide suitable for use in the acid-catalyzed decomposition for the production of carbonyl and hydroxy compounds, the amount of water added to said extract being limited to between from about 2 to about 50 wt. % based on the weight of the extract.

2. A process according to claim 1 wherein the aqueous alcoholic solvent is an aqueous methanolic solvent.

3. A process according to claim 2 wherein the amount of water added to the extract is limited to be from about 5 to about 30 wt. percent based on the weight of the extract.

4. A process according to claim 1 wherein the hydroperoxide is cyclohexylbenzene hydroperoxide.

5. A process according to claim 2 wherein the hydroperoxide is cyclohexylbenzene hydroperoxide.

6. A process according to claim 3 wherein the hydroperoxide is cyclohexylbenzene hydroperoxide.

7. A process according to claim 4 wherein the aqueous alcoholic solvent is formed using methanol.

8. A process according to claim 5 wherein the aqueous alcoholic solvent is formed using methanol.

9. A process according to claim 6 wherein the aqueous alcoholic solvent is formed using methanol.

* * * * *